United States Patent [19]
Weissman et al.

[11] Patent Number: 5,871,540
[45] Date of Patent: Feb. 16, 1999

[54] PATELLAR IMPLANT COMPONENT AND METHOD

[75] Inventors: Marc G. Weissman, Derby, Conn.; Mark A. Kester, Upper Saddle River, N.J.

[73] Assignee: Osteonics Corp., Allendale, N.J.

[21] Appl. No.: 690,306

[22] Filed: Jul. 30, 1996

[51] Int. Cl.[6] .................................................. A61F 2/38
[52] U.S. Cl. .................................................. 623/20
[58] Field of Search ................................. 623/16, 18, 20

[56] References Cited

U.S. PATENT DOCUMENTS

| | | |
|---|---|---|
| 3,927,423 | 12/1975 | Swanson . |
| 4,158,894 | 6/1979 | Worrell . |
| 4,285,070 | 8/1981 | Averill . |
| 4,309,778 | 1/1982 | Buechel et al. . |
| 4,650,490 | 3/1987 | Figgie, III . |
| 4,979,957 | 12/1990 | Hodorek . |
| 5,021,061 | 6/1991 | Wevers et al. . |
| 5,133,758 | 7/1992 | Hollister . |
| 5,246,469 | 9/1993 | Goodfellow et al. . |

Primary Examiner—David Isabella
Attorney, Agent, or Firm—Arthur Jacob

[57] ABSTRACT

A patellar component of a prosthetic knee joint includes a domed portion having a peak offset from the center of the patellar component for effecting compensation for the displacement of the mechanical joint line upon implant of the prosthetic knee joint so as to enable affixation of the patellar component within the natural patella with sufficient bone coverage while attaining appropriate sliding engagement of the patellar component with a patellar groove in the femoral component of the prosthetic knee joint during articulation of the knee.

12 Claims, 4 Drawing Sheets

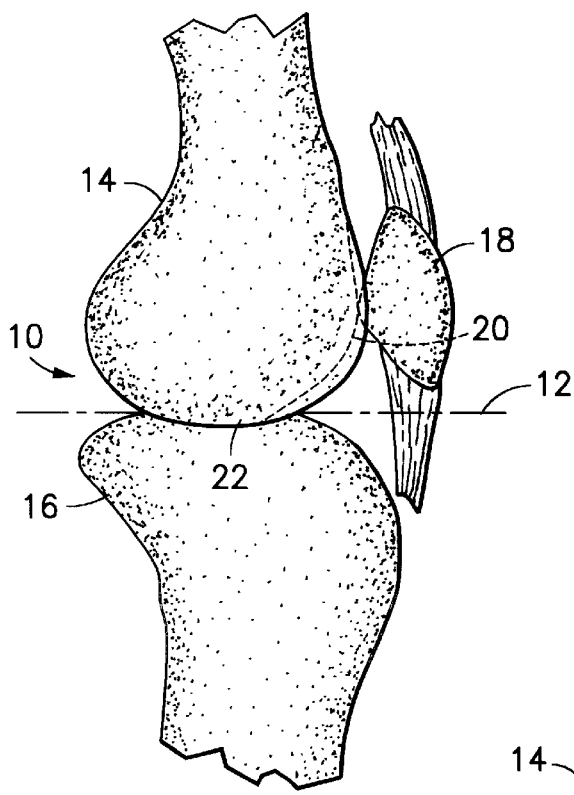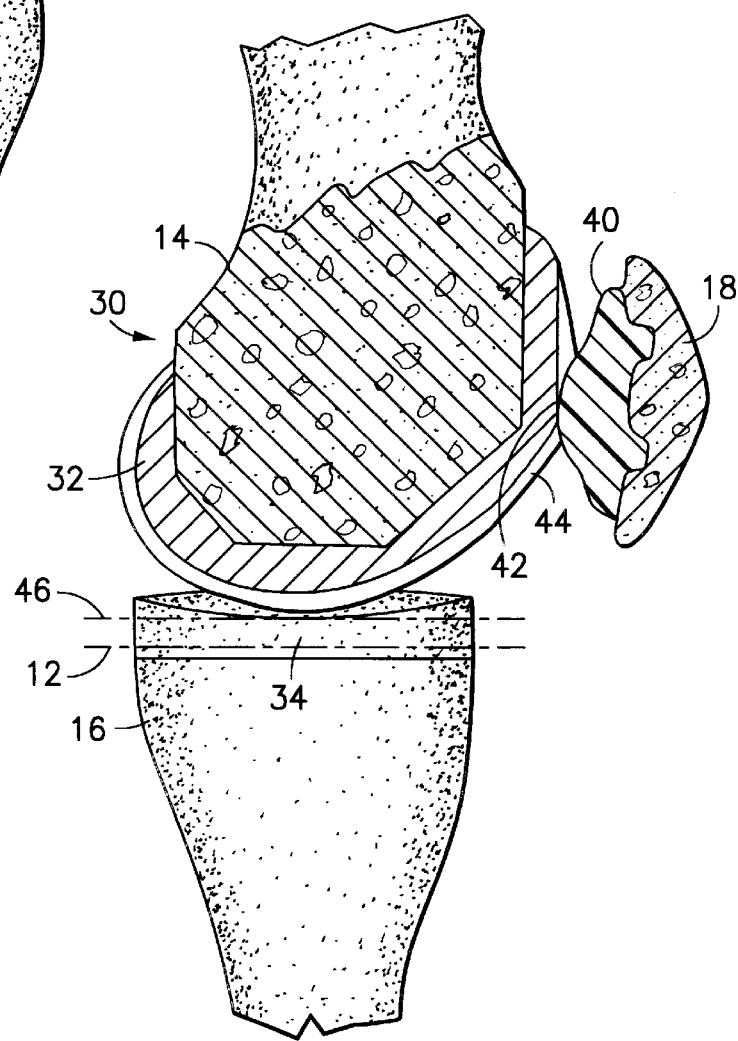
FIG.1
FIG.2
PRIOR ART

PATELLAR IMPLANT COMPONENT AND METHOD

The present invention relates generally to the replacement of the natural knee with a prosthetic knee joint and pertains, more specifically, to a patellar component and method for compensating for alteration of the location of the mechanical joint line of the knee resulting from the implant of a prosthetic knee joint.

Total knee replacement has become an important option available in the treatment of a natural knee joint which has become deteriorated as a result of injury or disease. Replacement of the natural knee with a prosthetic knee joint has become relatively commonplace and a variety of prosthetic knee implants, and related implant procedures, currently are available.

The replacement of a natural knee with currently available prosthetic knee implants usually results in alteration of the location of the mechanical joint line of the knee. Thus, upon completion of an implant procedure, the mechanical joint line may be raised or lowered with respect to the position formerly occupied in the natural knee. Such alteration of the location of the mechanical joint line has been shown to be detrimental to the functioning of the knee in that there may be a decrease in the range of motion of the knee and the possibility of accelerated wear of the patellar component of the prosthetic knee joint. While attempts by surgeons to compensate for alteration of the location of the mechanical joint line by adjusting the location of the patellar component relative to the bone of the natural patella have been moderately successful in improving the function of the knee by accomplishing an appropriate shift in patella-femoral articulation, such a procedure can compromise optimal bone coverage, with concomitant adverse effects on the function of the patella itself in the replaced knee joint.

The present invention provides a patellar component and method which compensate for alteration of the location of the mechanical joint line resulting from the implant of a prosthetic knee joint. As such, the present invention attains several objects and advantages, some of which are summarized as follows: Attains optimal bone coverage of the patella, with a concomitant improvement in stress distribution at the interface between the natural bone of the patella and the affixation where the patellar component is affixed to the bone of the natural patella, especially in instances where the patellar component is affixed with cement; reduces the potential for patella necrosis or fracture; facilitates the implant procedure, enabling proper placement and affixation of the patellar component with accuracy and in less time, to the benefit of the recipient of the prosthetic knee implant; improves patella-femoral alignment relative to the altered location of the mechanical joint line; enables an improved range of motion; improves stability of the prosthetic knee joint; enables improved quadriceps function; decreases any potential for patella subluxation; tends to reduce any anterior knee pain which might otherwise be experienced subsequent to the implant procedure; enhances performance of the prosthetic knee implant, facilitating movements experienced during daily activities, and especially those activities which produce high loads near the center of the patella, such as rising from a seated position and stair climbing; effectively decreases wear of the patellar component, thereby enabling an extended service life.

The above objects and advantages are attained by the present invention which may be described briefly as a patellar component for use in connection with a prosthetic knee joint in a knee implant procedure in which the location of the mechanical joint line of the knee after the implant procedure is altered by displacement in a longitudinal direction away from the location of the mechanical joint line prior to the implant procedure, the patellar component comprising: a basal portion extending longitudinally between an upper, superior edge and a lower, inferior edge, and extending laterally between opposite lateral and medial side edges, the basal portion having a lateral centerline extending laterally across the basal portion between the side edges and located longitudinally intermediate the upper and lower edges; and a domed portion raised altitudinally from the basal portion, in a rearward, posterior direction, the domed portion having a peak at a maximum altitudinal height from the basal portion, the peak being offset from the lateral centerline in a longitudinal direction an offset distance for compensating for the displacement of the mechanical joint line of the knee subsequent to the implant procedure. Further, the present invention includes an improvement in a method for implanting a prosthetic knee joint in which the location of the mechanical joint line of the knee after the implant procedure is altered by displacement in a longitudinal direction away from the location of the mechanical joint line prior to the implant procedure, the improvement comprising the steps of: implanting femoral and tibial components of the prosthetic knee joint; providing a patellar component having a basal portion and a domed portion raised altitudinally from the basal portion in a rearward, posterior direction, the basal portion having an upper, superior edge, a lower, inferior edge, and a lateral centerline extending laterally across the basal portion between opposite side edges and located longitudinally intermediate the upper and lower edges, the domed portion having a peak at a maximum altitudinal height from the basal portion, the peak being offset from the lateral centerline in a longitudinal direction an offset distance; and implanting the patellar component in the natural patella such that the offset distance of the peak of the domed portion of the patellar component compensates for the displacement of the mechanical joint line of the knee subsequent to the implant procedure.

The invention will be understood more fully, while still further objects and advantages will become apparent, in the following detailed description of preferred embodiments of the invention illustrated in the accompanying drawing, in which:

FIG. 1 is a largely diagrammatic side elevational view showing a natural knee joint;

FIG. 2 is a largely diagrammatic side elevational view showing a prior art patellar component in a prosthetic knee joint;

Figure 3:
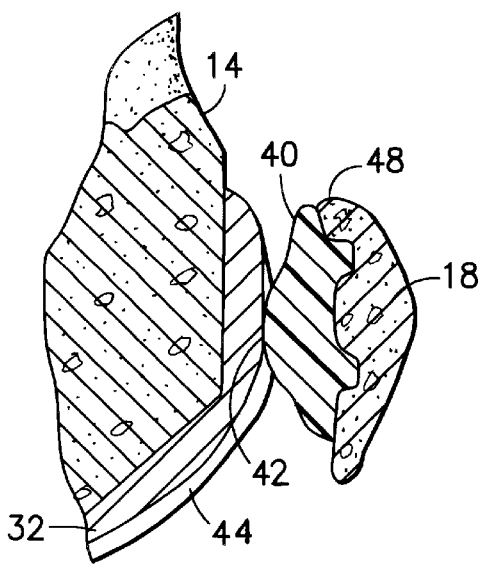
FIG. 3 is a fragmentary view of a portion of FIG. 2, with component parts in another position.

Referring now to the drawing, and especially to FIG. 1 thereof, a natural knee 10 includes a mechanical joint line 12 located between distal femur 14 and proximal tibia 16. A patella 18 is engaged with a patellar groove 20 located between the condyles 22 of the distal femur 14 so as to slide between the condyles 22 during articulation of the knee 10.

Turning now to FIG. 2, the distal femur 14 and the proximal tibia 16 have been prepared for the reception of a prosthetic knee joint 30, shown implanted between the prepared distal femur 14 and the prepared proximal tibia 16 and including a femoral component 32 and a tibial component 34, in a now conventional arrangement. A patellar component 40 has been implanted in the natural patella 18 and includes a posterior portion 42 which is domed for engaging a patellar groove 44 in the femoral component 32 for sliding movement within the patellar groove 44 during articulation of the prosthetic knee joint 30.

The implant procedure has required sacrifice of the posterior crusciate ligament, resulting in alteration of the location of mechanical joint line 46, now shown raised, that is, superior relative to the position of the mechanical joint line 12 of the natural knee 10. However, the position of the patella 18, relative to distal femur 14 remains unchanged, so that the position of the patella 18 relative to the mechanical joint line 46 is altered from the previous position of the patella 18 relative to the mechanical joint line 12. The altered relationship between the patella 18 and the mechanical joint line 46 has been found to be detrimental to the functioning of the knee in that there is a decrease in the range of motion of the knee and a potential for accelerated wear of the patellar component 40.

In an effort to avoid such detrimental effects, surgeons have attempted to compensate, interoperatively, for the altered position of the mechanical joint line 46 by adjusting the placement of the patellar component 40 in the natural bone of the patella 18 to bring the domed portion 42 of the patellar component 40 into appropriate alignment with the patellar groove 44. However, such attempts are, at best, approximations of the appropriate placement of the patellar component 40. Further, such adjustment can compromise optimal bone coverage by the natural bone of the patella 18. Thus, as seen in FIG. 3, a placement of the patellar component 40 in a raised, or superior, location within the patella 18, as opposed to the more longitudinally central location depicted in FIG. 2, in an effort to compensate for the raised position of the mechanical joint line 46, may move the domed portion 42 upwardly for more appropriate engagement with the patellar groove 44; however, the reduced amount of natural bone available adjacent upper edge 48 of the natural patella 18 does not permit optimal bone coverage in the vicinity of the upper edge 48 of the patellar component 40.

Figure 4:
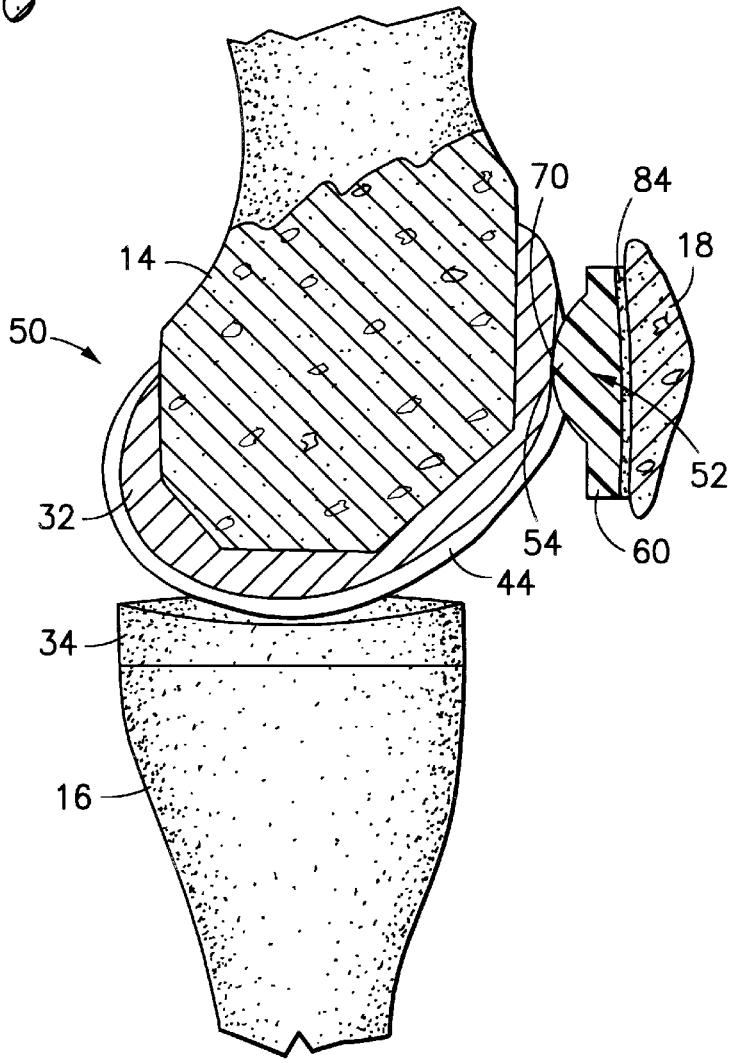
FIG. 4 is a largely diagrammatic side elevational view showing a patellar component constructed in accordance with the present invention in a prosthetic knee joint.

Referring now to FIG. 4, an alternate prosthetic knee joint 50 includes all of the same components as in prosthetic knee joint 30, with the exception that a patellar component 52 constructed in accordance with the present invention is seen implanted in patella 18 in place of conventional patellar component 40. As in patellar component 40, patellar component 52 includes a posterior portion 54 which is domed for engaging the patellar groove 44 in the femoral component 32 for sliding movement within the patellar groove 44 during articulation of the prosthetic knee joint 50; however, domed portion 54 is offset in the upward, or superior direction by a distance which places the domed portion 54 in position for appropriate engagement with the patellar groove 44. Thus, the offset placement of the domed portion 54 compensates for the upward, or superior displacement of the mechanical joint line 46 of the knee subsequent to the implant procedure.

Figure 5:
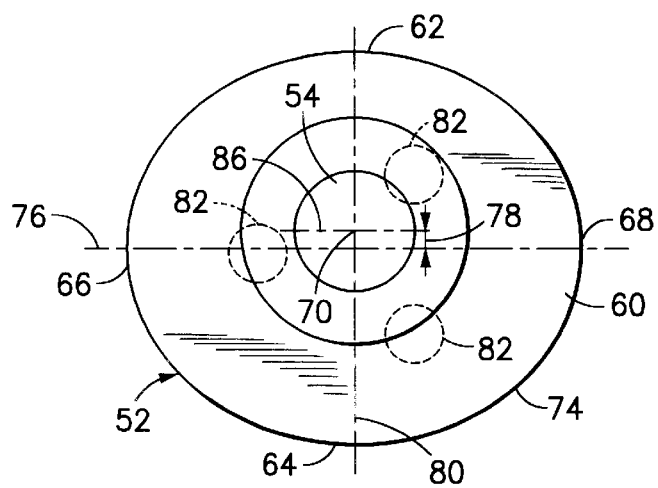
FIG. 5 is a plan view of the patellar component of FIG. 4
Figures 6, 7:
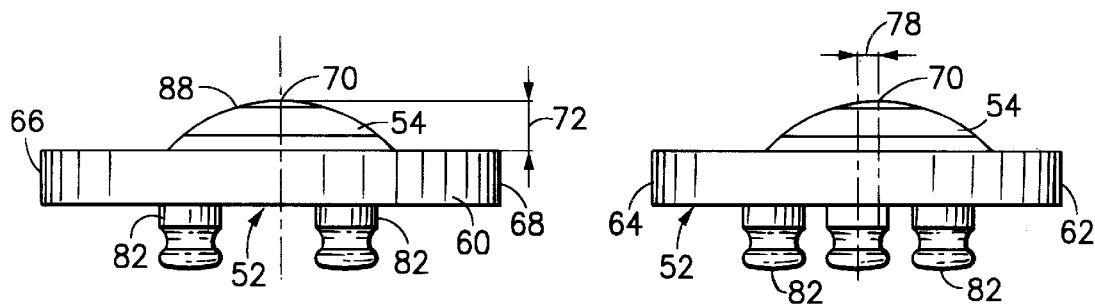
FIG. 6 is a front elevational view of the patellar component.
FIG. 7 is a side elevational view of the patellar component.

As best seen in FIGS. 5 through 7, as well as in FIG. 4, patellar component 52 includes a basal portion 60 extending longitudinally between an upper, or superior edge 62 and a longitudinally opposite lower, or inferior edge 64, and extending laterally between a lateral side edge 66 and a laterally opposite medial side edge 68. The domed portion 54 of the patellar component 52 is raised altitudinally from the basal portion 60, in a rearward, or posterior direction, and includes a peak 70 at a maximum altitudinal height 72 from the basal portion 60. The basal portion 60 has an outer perimeter 74 sized to fit within the bounds of the natural patella 18, and a lateral centerline 76 passes through the center of the basal portion 60 and extends laterally across the basal portion 60 between the opposite side edges 66 and 68, longitudinally intermediate the upper and lower edges 62 and 64. The peak 70 of the domed portion 54 is offset from the lateral centerline 76 in the upward, or superior direction by an offset distance 78 along a longitudinal centerline 80 extending longitudinally across the basal portion 60 between the opposite upper and lower edges 62 and 64 for compensating for the altered position of the mechanical joint line 46. Thus, the peak 70 is located between the lateral centerline 76 and the upper edge 62 of the basal portion 60. A plurality of affixation pegs 82 project from the basal portion 60 in a forward, or anterior direction and assist in the location and affixation of the patellar component 52 upon the natural patella 18. As seen in FIG. 4, in the present embodiment a cement mantle 84 secures the patellar component 52 to the natural bone of the patella 18.

Upon implant of the patellar component 52 in the natural patella 18, as illustrated in FIG. 4, the basal portion 60 of the patellar component 52 is located upon the patella 18 such that natural bone extends around the basal portion 60 of the patellar component 52 for sufficient bone coverage, while the peak 70 of the domed portion 54 is located for appropriate engagement with the patellar groove 44. The offset distance 78 is related to the parameters of the particular prosthetic knee joint 50 so that in carrying out the implant procedure the surgeon can locate the basal portion 60 well within the bounds of the natural bone of the patella 18, and the peak 70 of the domed portion 54 will be placed for appropriate engagement with the patellar groove 44. In a typical patellar component 52, the outer perimeter 74 of the basal portion 60 has a generally elliptical plan configuration, and the domed portion 54 is symmetrical about an axis of symmetry 86 passing through the peak 70, the domed portion 54 including an outer surface 88 having a generally semi-spherical surface contour configuration and the axis of symmetry 86 being offset from the lateral centerline 76 by the offset distance 78. Typical dimensions include a longitudinal span, or distance, between the upper edge 62 and the lower edge 64 in the range of about 30 mm to about 38 mm, and a lateral span, or distance, between the opposite side edges 66 and 68 in the range of about 32 mm to about 44 mm, with the offset distance 78 being about 1.5 mm. In the illustrated embodiment, the peak 70 of the domed portion 54 is offset in the upward, or superior direction. In those instances where alteration of the location of the mechanical joint line displaces the mechanical joint line in a downward, or inferior direction, the peak 70 of the domed portion 54 is offset from the lateral centerline 76 in a corresponding downward, or inferior direction to compensate for the altered, downwardly displaced location of the mechanical joint line.

Figure 8:
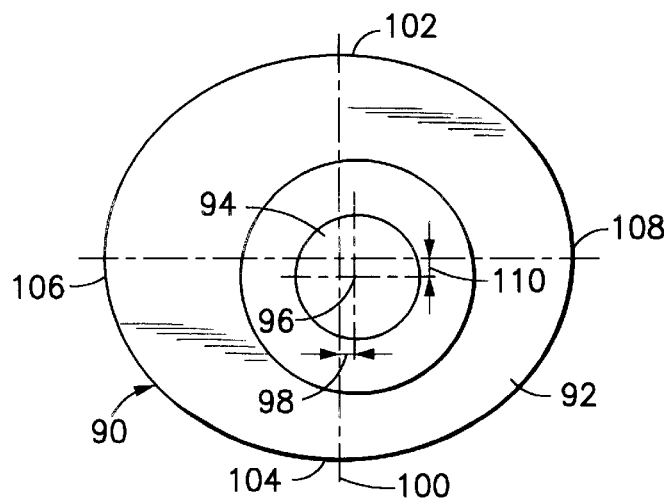
FIG. 8 is a plan view of another patellar component constructed in accordance with the invention.
Figures 9, 10:
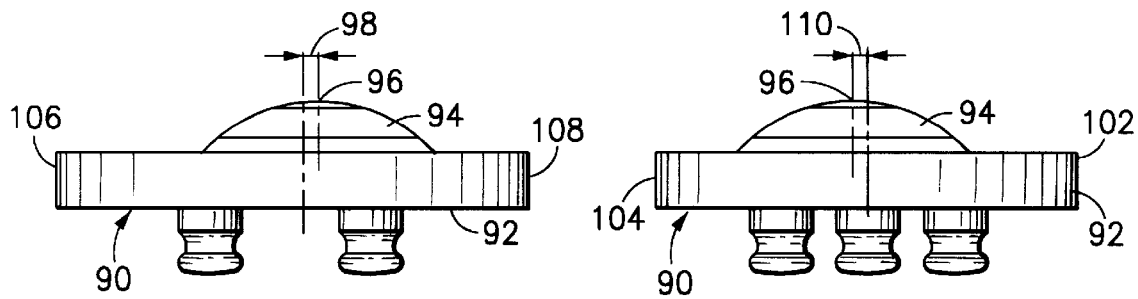
FIG. 9 is a front elevational view of the patellar component of FIG. 8.
FIG. 10 is a side elevational view of the patellar component.

Turning now to FIGS. 8 through 10, another patellar component constructed in accordance with the present invention is shown at 90. As in the earlier-described embodiment, patellar component 90 includes a basal portion 92 and a domed posterior portion 94. However, in the present patellar component 90, peak 96 of the domed portion 94 is offset laterally in the medial direction by a lateral offset distance 98 from a longitudinal centerline 100 which passes through the center of the basal portion 92 and extends longitudinally across the basal portion 92 between opposite upper and lower edges 102 and 104, respectively, and is located intermediate opposite lateral and medial side edges 106 and 108, respectively, as well as longitudinally downwardly by a longitudinal offset distance 110. The offset of the peak 96 of the domed portion 94 attained by the combined longitudinal offset distance 110 and lateral offset distance 98 compensates for any eccentricity of the loads on the patella 18 in the transverse, or horizontal plane. In a typical patellar component 90, the longitudinal span between the upper edge 102 and the lower edge 104 is in the range of about 30 mm to about 38 mm, and the lateral span between the opposite side edges 106 and 108 is in the range of about 32 mm to about 44 mm, with the magnitude of each of the offset distances 98 and 110 being about 1.5 mm.

It will be seen that the present invention attains the several objects and advantages summarized above, namely: Attains optimal bone coverage of the patella, with a concomitant improvement in stress distribution at the interface between the natural bone of the patella and the affixation where the patellar component is affixed to the bone of the natural patella, especially in instances where the patellar component is affixed with cement; reduces the potential for patella necrosis or fracture; facilitates the implant procedure, enabling proper placement and affixation of the patellar component with accuracy and in less time, to the benefit of the recipient of the prosthetic knee implant; improves patella-femoral alignment relative to the altered location of the mechanical joint line; enables an improved range of motion; improves stability of the prosthetic knee joint; enables improved quadriceps function; decreases any potential for patella subluxation; tends to reduce any anterior knee pain which might otherwise be experienced subsequent to the implant procedure; enhances performance of the prosthetic knee implant, facilitating movements experienced during daily activities, and especially those activities which produce high loads near the center of the patella, such as rising from a seated position and stair climbing; effectively decreases wear of the patellar component, thereby enabling an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A patellar component for use in connection with a prosthetic knee joint in a knee implant procedure in which the location of the mechanical joint line of the knee after the implant procedure is altered by displacement in a longitudinal direction away from the location of the mechanical joint line prior to the implant procedure, the patellar component comprising:

a basal portion extending longitudinally between an upper, superior edge and a lower, inferior edge, and extending laterally between opposite lateral and medial side edges, the basal portion having a lateral centerline extending laterally across the basal portion between the side edges and located longitudinally intermediate the upper and lower edges; and a domed portion raised altitudinally from the basal portion, in a rearward, posterior direction, the domed portion having a peak at a maximum altitudinal height from the basal portion, the peak being offset from the lateral centerline in a longitudinal direction an offset distance for compensating for the displacement of the mechanical joint line of the knee subsequent to the implant procedure.

2. The invention of claim 1 wherein the longitudinal direction is toward the upper, superior edge such that the peak of the domed portion is located between the lateral centerline and the upper, superior edge of the basal portion.

3. The invention of claim 1 wherein the domed portion is located on a longitudinal centerline extending longitudinally across the basal portion between the upper, superior edge and the lower, inferior edge and located intermediate the opposite lateral and medial side edges.

4. The invention of claim 1 wherein the domed portion is symmetrical about an axis of symmetry passing through the peak and the axis of symmetry is offset from the lateral centerline by the offset distance.

5. The invention of claim 1 wherein the domed portion includes an outer surface having a generally semi-spherical surface contour configuration.

6. The invention of claim 1 wherein the basal portion includes an outer perimeter having a generally elliptical plan configuration.

7. The invention of claim 6 wherein the longitudinal distance between the upper, superior edge and the lower, inferior edge is in the range of about 30 mm to about 38 mm, the lateral distance between the opposite side edges is in the range of about 32 mm to about 44 mm, and the offset distance is about 1.5 mm.

8. The invention of claim 1 wherein the basal portion includes a longitudinal centerline extending longitudinally across the basal portion between the upper and lower edges and located laterally intermediate the opposite side edges, and the peak of the domed portion is offset from the longitudinal centerline so as to be located at a further offset distance between the longitudinal centerline and the medial side edge.

9. The invention of claim 8 wherein the basal portion includes an outer perimeter having an elliptical plan configuration.

10. The invention of claim 9 wherein the longitudinal distance between the upper, superior edge and the lower, inferior edge is in the range of about 30 mm to about 38 mm, the lateral distance between the opposite side edges is in the range of about 32 mm to about 44 mm, the offset distance is about 1.5 mm, and the further offset distance is about 1.5 mm.

11. An improvement in a method for implanting a prosthetic knee joint in which the location of the mechanical joint line of the knee after the implant procedure is altered by displacement in a longitudinal direction away from the location of the mechanical joint line prior to the implant procedure, the improvement comprising the steps of:

implanting femoral and tibial components of the prosthetic knee joint;

providing a patellar component having a basal portion and a domed portion raised altitudinally from the basal portion in a rearward, posterior direction, the basal portion having an upper, superior edge, a lower, inferior edge, and a lateral centerline extending laterally across the basal portion between opposite side edges and located longitudinally intermediate the upper and lower edges, the domed portion having a peak at a maximum altitudinal height from the basal portion, the peak being offset from the lateral centerline in a longitudinal direction an offset distance; and implanting the patellar component in the natural patella such that the offset distance of the peak of the domed portion of the patellar component compensates for the displacement of the mechanical joint line of the knee subsequent to the implant procedure.

12. The invention of claim 11 wherein the displacement of mechanical joint line is in the upward, superior direction and the peak of the domed portion is located between the longitudinal centerline and the upper, superior edge of the basal portion of the patellar component such that implanting the patellar component locates the domed portion in appropriate position relative to the femoral component of the prosthetic knee joint.

* * * * *